United States Patent [19]
Turpen

[11] Patent Number: 5,811,653
[45] Date of Patent: Sep. 22, 1998

[54] VIRAL AMPLIFICATION OF RECOMBINANT MESSENGER RNA IN TRANSGENIC PLANTS

[75] Inventor: Thomas H. Turpen, Vacaville, Calif.

[73] Assignee: Biosource Technologies, Inc., Vacaville, Calif.

[21] Appl. No.: 176,414

[22] Filed: Dec. 29, 1993

Related U.S. Application Data

[63] Continuation-in-part of Ser. No. 997,733, Dec. 30, 1992, abandoned.

[51] Int. Cl.⁶ .............................. A01H 5/00; C12N 15/40; C12N 15/83; C12N 5/04
[52] U.S. Cl. .................... 800/205; 536/23.72; 536/24.1; 435/69.1; 435/172.3; 435/235.1; 435/320.1; 435/419
[58] Field of Search .......................... 800/205; 536/23.2, 536/23.72, 24.1; 530/350, 826; 435/69.1, 70.1, 172.3, 235.1, 320.1, 419

[56] References Cited

FOREIGN PATENT DOCUMENTS

| | | |
|---|---|---|
| B7 195 191 | 3/1992 | Australia . |
| A0 067 553 | 12/1982 | European Pat. Off. . |
| A0 425 004 | 5/1991 | European Pat. Off. . |
| A0 479 180 | 4/1992 | European Pat. Off. . |
| A0 573 767 | 12/1993 | European Pat. Off. . |
| WO A89 08145 | 9/1989 | WIPO . |
| WO A90 12107 | 10/1990 | WIPO . |
| WO A91 13994 | 9/1991 | WIPO . |

OTHER PUBLICATIONS

Raffo, Anthony J. and Dawson, William O. "Constructon of Tobacco Mosaic Virus Subgenomic Replicons That Are Replicated and Spread Systemically in Tobacco Plants". *Virology* 184: 277–289 (1991).
Joshi, Rajiv L. et al. "BSMV genome mediated expression of a foreign gene in dicot and monocot plant cells". *The EMBO Journal*, vol. 9: 2663–2669 (1990).
Joshi et al. 1991. FEBS Lett.: 1–8.
Takamatsu et al. 1987. EMBO J. 6: 307–11.
Larkins et al. 1985. J. Cell. Biochem. Suppl. O ( 9 Part C): 264.
Barton et al. 1987. Plant Physiol. 85:1103–9

*Primary Examiner*—David T. Fox
*Attorney, Agent, or Firm*—Albert P. Halluin; Howrey & Simon

[57] ABSTRACT

A novel method of over expressing genes in plants is provided. This method is based on the RNA amplification properties of plus strand RNA viruses of plants. A chimeric multicistronic gene is constructed containing a plant promoter, viral replication origins, a viral movement protein gene, and one or more foreign genes under control of viral subgenomic promoters. Plants containing one or more of these recombinant RNA transcripts are inoculated with helper virus. In the presence of helper virus recombinant transcripts are replicated producing high levels of foreign gene RNA.

Sequences are provided for the high level expression of the enzyme chloramphenicol acetyltransferase in tobacco plants by replicon RNA amplification with helper viruses and movement protein genes derived from the tobamovirus group.

20 Claims, 7 Drawing Sheets

TRANSGENE (cDNA)

↓ TRANSCRIPTION

TRANSCRIPT (RNA)

↓ RNA PROCESSING AND RNA REPLICATION

REPLICON (RNA)

P = PROMOTER
5'RO = 5' REPLICATION ORIGIN
FG = SEQUENCE CODING FOR FOREIGN GENE AS WELL AS OTHER SEQUENCES. DOES NOT CODE FOR COMPLETE SET OF VIRAL REPLICATION PROTEINS REQUIRED FOR REPLICATION.
3' RO = 3' REPLICATION ORIGIN
TT = TRANSCRIPTION TERMINATION SEQUENCE

| 35S Promoter | 5' nc | 30K-MP gene | CAT | 3' nc | rz | nc: non-coding region
rz: ribozyme pBGC272    3046 base pairs    Unique Sites

287 EarI
341 BspMI
344 BsaI
689 HincII
701 HgiAI
707 DrdI
716 AccI
923 PshAI
982 MmeI
1016 EcoRV
1124 MunI
1176 NdeI
1310 BspHI
1356 HindIII
1386 Cfr10I
1507 AlwNI
1938 BspDI
1938 ClaI
2234 BspEI
2238 EcoRI
2464 PflMI
2503 EaeI
2503 MseI
2786 NsiI
2819 AflIII
2820 DraIII
2820 PmlI
2829 BsiWI
2829 SplI
2888 HhaI
2888 HinPI
2946 BstBI
3029 PstI
3035 SmaI
3035 XmaI
3041 BamHI

5,811,653

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
        ( A ) LENGTH: 1825 base pairs
        ( B ) TYPE: nucleic acid
        ( C ) STRANDEDNESS: unknown
        ( D ) TOPOLOGY: unknown ( i i ) MOLECULE TYPE: RNA (genomic)

( i x ) FEATURE:
        ( A ) NAME/KEY: CDS
        ( B ) LOCATION: 70..1527

( x i ) SEQUENCE DESCRIPTION: SEQ ID NO:1:

```
GUAUUUUUAC  AACAAUUACC  AACAACAACA  AACAACAAAC  AACAUUACAA  UUACUAUUUA         60

CAAUUACAU AUG GCU CUA GUU GUU AAA GGA AAA GUG AAU AUC AAU GAG              108
          Met Ala Leu Val Val Lys Gly Lys Val Asn Ile Asn Glu
            1               5                   10

UUU AUC GAC CUG ACA AAA AUG GAG AAG AUC UUA CCG UCG AUG UUU ACC            156
Phe Ile Asp Leu Thr Lys Met Glu Lys Ile Leu Pro Ser Met Phe Thr
     15                  20                  25

CCU GUA AAG AGU GUU AUG UGU UCC AAA GUU GAU AAA AUA AUG GUU CAU            204
Pro Val Lys Ser Val Met Cys Ser Lys Val Asp Lys Ile Met Val His
 30                      35                  40                  45

GAG AAU GAG UCA UUG UCA GAG GUG AAC CUU UUU AAA GGA GUU AAG CUU            252
Glu Asn Glu Ser Leu Ser Glu Val Asn Leu Phe Lys Gly Val Lys Leu
                  50                      55                  60

AUU GAU AGU GGA UAC GUC UGU UUA GCC GGU UUG GUC GUC ACG GGC GAG            300
Ile Asp Ser Gly Tyr Val Cys Leu Ala Gly Leu Val Val Thr Gly Glu
                 65                      70                  75

UGG AAC UUG CCU GAC AAU UGC AGA GGA GGU GUG AGC GUG UGU CUG GUG            348
Trp Asn Leu Pro Asp Asn Cys Arg Gly Gly Val Ser Val Cys Leu Val
```

```
                80                              85                              90
GAC  AAA  AGG  AUG  GAA  AGA  GCC  GAC  GAG  GCC  ACU  CUC  GGA  UCU  UAC  UAC    396
Asp  Lys  Arg  Met  Glu  Arg  Ala  Asp  Glu  Ala  Thr  Leu  Gly  Ser  Tyr  Tyr
     95                      100                     105

ACA  GCA  GCU  GCA  AAG  AAA  AGA  UUU  CAG  UUC  AAG  GUC  GUU  CCC  AAU  UAU    444
Thr  Ala  Ala  Ala  Lys  Lys  Arg  Phe  Gln  Phe  Lys  Val  Val  Pro  Asn  Tyr
110                      115                     120                          125

GCU  AUA  ACC  ACC  CAG  GAC  GCG  AUG  AAA  AAC  GUC  UGG  CAA  GUU  UUA  GUU    492
Ala  Ile  Thr  Thr  Gln  Asp  Ala  Met  Lys  Asn  Val  Trp  Gln  Val  Leu  Val
                    130                     135                          140

AAU  AUU  AGA  AAU  GUG  AAG  AUG  UCA  GCG  GGU  UUC  UGU  CCG  CUU  UCU  CUG    540
Asn  Ile  Arg  Asn  Val  Lys  Met  Ser  Ala  Gly  Phe  Cys  Pro  Leu  Ser  Leu
               145                      150                          155

GAG  UUU  GUG  UCG  GUG  UGU  AUU  GUU  UAU  AGA  AAU  AAU  AUA  AAA  UUA  GGU    588
Glu  Phe  Val  Ser  Val  Cys  Ile  Val  Tyr  Arg  Asn  Asn  Ile  Lys  Leu  Gly
          160                      165                     170

UUG  AGA  GAG  AAG  AUU  ACA  AAC  GUG  AGA  GAC  GGA  GGG  CCC  AUG  GAA  CUU    636
Leu  Arg  Glu  Lys  Ile  Thr  Asn  Val  Arg  Asp  Gly  Gly  Pro  Met  Glu  Leu
     175                      180                     185

ACA  GAA  GAA  GUC  GUU  GAU  GAG  UUC  AUG  GAA  GAU  GUC  CCU  AUG  UCG  AUC    684
Thr  Glu  Glu  Val  Val  Asp  Glu  Phe  Met  Glu  Asp  Val  Pro  Met  Ser  Ile
190                      195                     200                          205

AGG  CUU  GCA  AAG  UUU  CGA  UCU  CGA  ACC  GGA  AAA  AAG  AGU  GAU  GUC  CGC    732
Arg  Leu  Ala  Lys  Phe  Arg  Ser  Arg  Thr  Gly  Lys  Lys  Ser  Asp  Val  Arg
                    210                     215                          220

AAA  GGG  AAA  AAU  AGU  AGU  AAU  GAU  CGG  UCA  GUG  CCG  AAC  AAG  AAC  UAU    780
Lys  Gly  Lys  Asn  Ser  Ser  Asn  Asp  Arg  Ser  Val  Pro  Asn  Lys  Asn  Tyr
               225                      230                     235

AGA  AAU  GUU  AAG  GAU  UUU  GGA  GGA  AUG  AGU  UUU  AAA  AAG  AAU  AAU  UUA    828
Arg  Asn  Val  Lys  Asp  Phe  Gly  Gly  Met  Ser  Phe  Lys  Lys  Asn  Asn  Leu
          240                      245                     250

AUC  GAU  GAU  GAU  UCG  GAG  GCU  ACU  GUC  GCC  GAA  UCG  GAU  UCG  UUU  UAA    876
Ile  Asp  Asp  Asp  Ser  Glu  Ala  Thr  Val  Ala  Glu  Ser  Asp  Ser  Phe   *
     255                      260                     265

AUA  CGC  UCG  ACG  AGA  UUU  UCA  GGA  GCU  AAG  GAA  GCU  AAA  AUG  GAG  AAA    924
Ile  Arg  Ser  Thr  Arg  Phe  Ser  Gly  Ala  Lys  Glu  Ala  Lys  Met  Glu  Lys
270                      275                     280                          285

AAA  AUC  ACU  GGA  UAU  ACC  ACC  GUU  GAU  AUA  UCC  CAA  UCG  CAU  CGU  AAA    972
Lys  Ile  Thr  Gly  Tyr  Thr  Thr  Val  Asp  Ile  Ser  Gln  Ser  His  Arg  Lys
                    290                     295                          300

GAA  CAU  UUU  GAG  GCA  UUU  CAG  UCA  GUU  GCU  CAA  UGU  ACC  UAU  AAC  CAG   1020
Glu  His  Phe  Glu  Ala  Phe  Gln  Ser  Val  Ala  Gln  Cys  Thr  Tyr  Asn  Gln
               305                      310                     315

ACC  GUU  CAG  CUG  GAU  AUU  ACG  GCC  UUU  UUA  AAG  ACC  GUA  AAG  AAA  AAU   1068
Thr  Val  Gln  Leu  Asp  Ile  Thr  Ala  Phe  Leu  Lys  Thr  Val  Lys  Lys  Asn
          320                      325                     330

AAG  CAC  AAG  UUU  UAU  CCG  GCC  UUU  AUU  CAC  AUU  CUU  GCC  CGC  CUG  AUG   1116
Lys  His  Lys  Phe  Tyr  Pro  Ala  Phe  Ile  His  Ile  Leu  Ala  Arg  Leu  Met
     335                      340                     345

AAU  GCU  CAU  CCG  GAA  UUC  CGU  AUG  GCA  AUG  AAA  GUU  UUC  CAU  GAG  CAA   1164
Asn  Ala  His  Pro  Glu  Phe  Arg  Met  Ala  Met  Lys  Val  Phe  His  Glu  Gln
350                      355                     360                          365

ACU  GAA  ACG  UUU  UCA  UCG  CUC  UGG  AGU  GAA  UAC  CAC  GAC  GAU  UUC  CGG   1212
Thr  Glu  Thr  Phe  Ser  Ser  Leu  Trp  Ser  Glu  Tyr  His  Asp  Asp  Phe  Arg
                    370                     375                          380

CAG  UUU  CUA  CAC  AUA  UAU  UCG  CAA  GAU  GUG  GCG  UGU  UAC  GGU  GAA  AAC   1260
Gln  Phe  Leu  His  Ile  Tyr  Ser  Gln  Asp  Val  Ala  Cys  Tyr  Gly  Glu  Asn
               385                      390                     395

CUG  GCC  UAU  UUC  CCU  AAA  GGG  UUU  AUU  GAG  AAU  AUG  UUU  UUC  GUC  UCA   1308
Leu  Ala  Tyr  Phe  Pro  Lys  Gly  Phe  Ile  Glu  Asn  Met  Phe  Phe  Val  Ser
```

```
                          400                           405                                    410
GCC  AAU  CCC  UGG  GUG  AGU  UUC  ACC  AGU  UUU  GAU  UUA  AAC  GUG  GCC  AAU     1356
Ala  Asn  Pro  Trp  Val  Ser  Phe  Thr  Ser  Phe  Asp  Leu  Asn  Val  Ala  Asn
     415                      420                     425

AUG  GAC  AAC  UUC  UUC  GCC  CCC  GUU  UUC  ACC  AUG  GGC  AAA  UAU  UAU  ACG     1404
Met  Asp  Asn  Phe  Phe  Ala  Pro  Val  Phe  Thr  Met  Gly  Lys  Tyr  Tyr  Thr
430                      435                     440                          445

CAA  GGC  GAC  AAG  GUG  CUG  AUG  CCG  CUG  GCG  AUU  CAG  GUU  CAU  CAU  GCC     1452
Gln  Gly  Asp  Lys  Val  Leu  Met  Pro  Leu  Ala  Ile  Gln  Val  His  His  Ala
                    450                     455                          460

GUC  UGU  GAU  GGC  UUC  CAU  GUC  GGC  AGA  AUG  CUU  AAU  GAA  UUA  CAA  CAG     1500
Val  Cys  Asp  Gly  Phe  His  Val  Gly  Arg  Met  Leu  Asn  Glu  Leu  Gln  Gln
               465                     470                     475

UAC  UGC  GAU  GAG  UGG  CAG  GGC  GGG  GCG  UAAUUUUUUU  AAGGCAGUUA               1547
Tyr  Cys  Asp  Glu  Trp  Gln  Gly  Gly  Ala
               480                     485

UUGGUGCCCU  UAAACGCCUG  GUGCUACGCC  UGAAUAAGUG  AUAAUAAGCG  GAUGAAUGGC            1607

AGAAAUUCGU  CGAGGGUAGU  CAAGAUGCAU  AAUAAAUAAC  GGAUUGUGUC  CGUAAUCACA            1667

CGUGGUGCGU  ACGAUAACGC  AUAGUGUUUU  UCCUCCACU   UAAAUCGAAG  GGUUGUGUCU            1727

UGGAUCGCGC  GGGUCAAAUG  UAUAUGGUUC  AUAUACAUCC  GCAGGCACGU  AAUAAAGCGA            1787

GGGGUUCGAA  UCCCCCCGUU  ACCCCCGGUA  GGGGCCCA                                     1825
```

(2) INFORMATION FOR SEQ ID NO:2:

(i) SEQUENCE CHARACTERISTICS:
        (A) LENGTH: 268 amino acids
        (B) TYPE: amino acid
        (D) TOPOLOGY: linear (ii) MOLECULE TYPE: protein (xi) SEQUENCE DESCRIPTION: SEQ ID NO:2:

```
Met  Ala  Leu  Val  Val  Lys  Gly  Lys  Val  Asn  Ile  Asn  Glu  Phe  Ile  Asp
 1                   5                    10                       15

Leu  Thr  Lys  Met  Glu  Lys  Ile  Leu  Pro  Ser  Met  Phe  Thr  Pro  Val  Lys
               20                   25                       30

Ser  Val  Met  Cys  Ser  Lys  Val  Asp  Lys  Ile  Met  Val  His  Glu  Asn  Glu
          35                   40                       45

Ser  Leu  Ser  Glu  Val  Asn  Leu  Phe  Lys  Gly  Val  Lys  Leu  Ile  Asp  Ser
     50                   55                       60

Gly  Tyr  Val  Cys  Leu  Ala  Gly  Leu  Val  Val  Thr  Gly  Glu  Trp  Asn  Leu
 65                       70                   75                           80

Pro  Asp  Asn  Cys  Arg  Gly  Gly  Val  Ser  Val  Cys  Leu  Val  Asp  Lys  Arg
                    85                   90                           95

Met  Glu  Arg  Ala  Asp  Glu  Ala  Thr  Leu  Gly  Ser  Tyr  Tyr  Thr  Ala  Ala
               100                  105                      110

Ala  Lys  Lys  Arg  Phe  Gln  Phe  Lys  Val  Val  Pro  Asn  Tyr  Ala  Ile  Thr
          115                  120                      125

Thr  Gln  Asp  Ala  Met  Lys  Asn  Val  Trp  Gln  Val  Leu  Val  Asn  Ile  Arg
     130                      135                      140

Asn  Val  Lys  Met  Ser  Ala  Gly  Phe  Cys  Pro  Leu  Ser  Leu  Glu  Phe  Val
145                      150                      155                      160

Ser  Val  Cys  Ile  Val  Tyr  Arg  Asn  Asn  Ile  Lys  Leu  Gly  Leu  Arg  Glu
               165                      170                      175

Lys  Ile  Thr  Asn  Val  Arg  Asp  Gly  Gly  Pro  Met  Glu  Leu  Thr  Glu  Glu
               180                      185                      190
```

-continued

| Val | Val | Asp | Glu | Phe | Met | Glu | Asp | Val | Pro | Met | Ser | Ile | Arg | Leu | Ala |
|     |     | 195 |     |     |     |     | 200 |     |     |     |     | 205 |     |     |     |

| Lys | Phe | Arg | Ser | Arg | Thr | Gly | Lys | Lys | Ser | Asp | Val | Arg | Lys | Gly | Lys |
|     | 210 |     |     |     |     | 215 |     |     |     |     | 220 |     |     |     |     |

| Asn | Ser | Ser | Asn | Asp | Arg | Ser | Val | Pro | Asn | Lys | Asn | Tyr | Arg | Asn | Val |
| 225 |     |     |     |     | 230 |     |     |     |     | 235 |     |     |     |     | 240 |

| Lys | Asp | Phe | Gly | Gly | Met | Ser | Phe | Lys | Lys | Asn | Asn | Leu | Ile | Asp | Asp |
|     |     |     |     | 245 |     |     |     |     | 250 |     |     |     |     | 255 |     |

| Asp | Ser | Glu | Ala | Thr | Val | Ala | Glu | Ser | Asp | Ser | Phe |
|     |     |     | 260 |     |     |     |     | 265 |     |     |     |

(2) INFORMATION FOR SEQ ID NO:3:

(i) SEQUENCE CHARACTERISTICS:
    (A) LENGTH: 217 amino acids
    (B) TYPE: amino acid
    (D) TOPOLOGY: linear (ii) MOLECULE TYPE: protein (xi) SEQUENCE DESCRIPTION: SEQ ID NO:3:

| Ile | Arg | Ser | Thr | Arg | Phe | Ser | Gly | Ala | Lys | Glu | Ala | Lys | Met | Glu | Lys |
| 1   |     |     |     | 5   |     |     |     |     | 10  |     |     |     |     | 15  |     |

| Lys | Ile | Thr | Gly | Tyr | Thr | Thr | Val | Asp | Ile | Ser | Gln | Ser | His | Arg | Lys |
|     |     |     | 20  |     |     |     |     | 25  |     |     |     |     | 30  |     |     |

| Glu | His | Phe | Glu | Ala | Phe | Gln | Ser | Val | Ala | Gln | Cys | Thr | Tyr | Asn | Gln |
|     |     | 35  |     |     |     |     | 40  |     |     |     |     | 45  |     |     |     |

| Thr | Val | Gln | Leu | Asp | Ile | Thr | Ala | Phe | Leu | Lys | Thr | Val | Lys | Lys | Asn |
|     | 50  |     |     |     |     | 55  |     |     |     |     | 60  |     |     |     |     |

| Lys | His | Lys | Phe | Tyr | Pro | Ala | Phe | Ile | His | Ile | Leu | Ala | Arg | Leu | Met |
| 65  |     |     |     |     | 70  |     |     |     |     | 75  |     |     |     |     | 80  |

| Asn | Ala | His | Pro | Glu | Phe | Arg | Met | Ala | Met | Lys | Val | Phe | His | Glu | Gln |
|     |     |     |     | 85  |     |     |     |     | 90  |     |     |     |     | 95  |     |

| Thr | Glu | Thr | Phe | Ser | Ser | Leu | Trp | Ser | Glu | Tyr | His | Asp | Asp | Phe | Arg |
|     |     |     | 100 |     |     |     |     | 105 |     |     |     |     | 110 |     |     |

| Gln | Phe | Leu | His | Ile | Tyr | Ser | Gln | Asp | Val | Ala | Cys | Tyr | Gly | Glu | Asn |
|     |     | 115 |     |     |     |     | 120 |     |     |     |     | 125 |     |     |     |

| Leu | Ala | Tyr | Phe | Pro | Lys | Gly | Phe | Ile | Glu | Asn | Met | Phe | Phe | Val | Ser |
|     | 130 |     |     |     |     | 135 |     |     |     |     | 140 |     |     |     |     |

| Ala | Asn | Pro | Trp | Val | Ser | Phe | Thr | Ser | Phe | Asp | Leu | Asn | Val | Ala | Asn |
| 145 |     |     |     |     | 150 |     |     |     |     | 155 |     |     |     |     | 160 |

| Met | Asp | Asn | Phe | Phe | Ala | Pro | Val | Phe | Thr | Met | Gly | Lys | Tyr | Tyr | Thr |
|     |     |     |     | 165 |     |     |     |     | 170 |     |     |     |     | 175 |     |

| Gln | Gly | Asp | Lys | Val | Leu | Met | Pro | Leu | Ala | Ile | Gln | Val | His | His | Ala |
|     |     |     | 180 |     |     |     |     | 185 |     |     |     |     | 190 |     |     |

| Val | Cys | Asp | Gly | Phe | His | Val | Gly | Arg | Met | Leu | Asn | Glu | Leu | Gln | Gln |
|     |     | 195 |     |     |     |     | 200 |     |     |     |     | 205 |     |     |     |

| Tyr | Cys | Asp | Glu | Trp | Gln | Gly | Gly | Ala |
|     | 210 |     |     |     |     | 215 |     | 217 |

VIRAL AMPLIFICATION OF RECOMBINANT MESSENGER RNA IN TRANSGENIC PLANTS

CROSS-REFERENCE TO RELATED APPLICATIONS

The present application is a continuation-in-part of application Ser. No. 997,733 filed Dec. 30, 1992, now abandoned.

BACKGROUND OF THE INVENTION

The present invention relates to the field of genetically engineering transgenic plants. More specifically, the invention relates to the use of viral RNA to achieve high level expression of foreign genes in plants.

The use of transgenic plants for high level expression of foreign genes has been targeted as an inexpensive means for mass producing desired products. All higher plants are photoautotrophic, requiring only $CO_2$, $H_2O$, $NO_3^{-1}$, $SO_4^{-2}$, $PO_4^{-3}$ and trace amounts of other elements for growth. From these inexpensive starting materials, plants are capable of synthesizing a variety of valuable products. Progress in utilizing transgenic plants as low cost factories will depend on both the characterization of biosynthetic pathways and on the further development of gene expression technologies.

In the past decade, a number of techniques have been developed to transfer genes into plants (Potrykus, I., *Annual Rev. Plant Physiol. Plant Mol. Biol.* 42:205–225 (1991)). For example, chromosomally integrated transgenes have been expressed by a variety of promoters offering developmental control of gene expression. (Walden and Schell, *Eur. J. Biochem.* 192:563–576 (1990)). This technology has been used primarily to improve certain agronomic traits such as disease resistance or food quality. (Joshi and Joshi, *Febs. Lett.* 281:1–8 (1991)). However, the utility of known trans-gene methodology is limited by 1) the difficulty of obtaining high level expression of individual transgenes 2) the lack of means necessary for coordinating control of several trans-genes in an individual plant 3) the lack of means to enable precise temporal control of gene expression and 4) the lack of adequate means to enable shutting off introduced genes in the uninduced state (Walden and Schell, *Eur. J. Biochem* 192:563–576 (1990)).

The most highly expressed genes in plants are encoded in plant RNA viral genomes. Many RNA viruses have gene expression levels or host ranges that make them useful for development as commercial vectors. (Ahlquist, P., and Pacha, R. F., *Physiol. Plant.* 79:163–167 (1990), Joshi, R. L., and Joshi, V., *FEBS Lett.* 281:1–8 (1991), Turpen, T. H., and Dawson, W. O., Amplification, movement and expression of genes in plants by viral-based vectors, *Transgenic plants: fundamentals and applications* (A. Hiatt, ed.), Marcel Dekker, Inc., New York, pp. 195–217. (1992)). For example, tobacco (*Nicotiana tabacum*) accumulates approximately 10 mg of tobacco mosaic tombamovirus (TMV) per gram of fresh-weight tissue 7–14 days after inoculation. TMV coat protein synthesis can represent 70% of the total cellular protein synthesis and can constitute 10% of the total leaf dry weight. A single specific RNA transcript can accumulate to 10% of the total leaf mRNA. This transcript level is over two orders of magnitude higher than the transcription level observed for chromosomally integrated genes using conventional plant genetic engineering technology. This level of foreign gene expression has not yet been obtained using the prior art viral vectors in plants.

Most plant viruses contain genomes of plus sense RNA (messenger RNA polarity) (Zaitlin and Hull, *Ann. Rev. Plant Physiol.* 38:291–315 (1987)). Plus sense plant viruses are a very versatile class of viruses to develop as gene expression vectors since there are a large number of strains from some 22 plus sense viral groups which are compatible with a wide number of host plant species. (Martelli, G. P., *Plant Disease* 76:436 (1992)). In addition, an evolutionarily related RNA-dependent RNA polymerase is encoded by each of these strains. This enzyme is responsible for genome replication and mRNA synthesis resulting in some of the highest levels of gene expression known in plants.

In order to develop a plant virus as a gene vector, one must be able to manipulate molecular clones of viral genomes and retain the ability to generate infectious recombinants. The techniques required to genetically engineer RNA viruses have progressed rapidly. If the virus is an RNA virus, the virus is generally cloned as a cDNA and inserted into a plasmid. The plasmid is used to make all of the constructions. The genome of many plus sense RNA viruses can be manipulated as plasmid DNA copies and then transcribed in vitro to produce infectious RNA molecules (reviewed in Turpen and Dawson, Transgenic Plants, Fundamentals and Applications, Marcel Dekker, New York, pp 195–217 (1992)).

The interaction of plants with viruses presents unique opportunities for the production of complex molecules as typified by the TMV/tobacco system (Dawson, W. O., *Virology* 186:359–367 (1992)). Extremely high levels of viral nucleic acids and/or proteins accumulate in infected cells in a brief period of time. The virus catalyzes rapid cell-to-cell movement of its genome throughout the plant, with no significant tissue tropism. The infection is maintained throughout the life of the plant. The plants are not significantly adversely affected by the viral infection since the virus causes little or no general cytotoxicity or specific suppression of host gene expression.

The tobacco mosaic tobamovirus is of particular interest to the instant invention in light of its ability to express genes at high levels in plants. TMV is a member of the tobamovirus group. TMV virions are 300 nm×18 nm tubes with a 4 nm-diameter hollow canal, and consist of 2140 units of a single structural protein helically wound around a single RNA molecule. The genome is a 6395 base plus-sense RNA. The 5'-end is capped and the 3'-end contains a series of pseudoknots and a tRNA-like structure that will specifically accept histidine. The genomic RNA functions as mRNA for the production of proteins involved in viral replication: a 126-kDa protein that initiates 68 nucleotides from the 5'-terminus and a 183-kDa protein synthesized by readthrough of an amber termination codon approximately 10% of the time (FIG. 1). Only the 183-kDa and 126-kDa viral proteins are required for TMV replication in trans. (Ogawa, T., Watanabe, Y., Meshi, T., and Okada, Y., *Virology* 185:580–584 (1991)). Additional proteins are translated from subgenomic size mRNA produced during replication (reviewed in Dawson, W. O., *Adv. Virus Res.* 38:307–342 (1990)). The 30-kDa protein is required for cell-to-cell movement; the 17.5-kDa capsid protein is the single viral structural protein. The function of the predicted 54-kDa protein is unknown.

The minimal sequences required in cis for TMV replication are located at the extreme 5' and 3' noncoding regions (replication origins), as determined by analysis of deletion mutants in plant protoplasts (Takamatsu, N., et al., *J. Virol.* 64:3686–3693 (1990), Takamatsu, N., et al., *J. Virol.* 65:1619–1622 (1991)). In whole plants, helper-dependent RNA replicons, constructed by deletion of most of the 126/183-kDa replication protein sequence and most of the 30-kDa movement protein sequence, are replicated and spread systemically in the presence of wild type TMV (Raffo A. J., and Dawson W. O., *Virology* 184:277–289 (1991)).

Turpen, et al. discloses a simple and reliable gene transfer method wherein cDNA of TMV is engineered into *A. tumefaciens* for expression in plant cells (Turpen, T. H., Ph.D. Dissertation, University of California, Riverside, pp. 88–105 (1992)). This method provides an alternative to the use of synthetic infectious transcripts to inoculate plants based on host transcription of viral cDNA in vivo. Turpen showed successful transfection of tobacco (*N. tabacum* cv. Xanthi and Xanthi/nc) with wild type and defective viral genomes using this methodology.

Transfection also occurs spontaneously in transgenic lines containing defective or wild type cDNA of TMV integrated chromosomally (Turpen, T. H., Ph.D. Dissertation, University of California, Riverside, pp. 106–132 (1992), Yamaya, J., et al., *Mol. Gen. Genet.* 211:520–525 (1988)). Thus, once chromosomally integrated, viral replication can be derived from the process of host cell transcription.

Plant virus infections are initiated by mechanical damage to the plant cell wall. Following replication in the initially wounded cells, progeny viruses spread over short distances (cell-to-cell movement) before entering vascular tissue for long distance movement. Studies with chimeric tobamoviruses indicate that the coat protein is required for efficient long distance movement. However, a virus where the coat protein has been deleted or inactivated moves over short distances as does wild type virus (Dawson W. O. and Hilf, M. E., *Ann. Rev. Plant Physiol. Plant Mol. Biol.* 43:527–555 (1992)).

In the case of TMV, functional 30-kDa movement protein is absolutely required for cell-to-cell movement in whole plants, but can be deleted or inactivated without affecting replication in protoplasts or inoculated leaves (reviewed in Citovsky, V., Zambryski, P., *BioEssays* 13:373–379 (1991) and Deom, C. M., Lapidot, M., and Beachy, R. N., *Cell* 69:221–224 (1992)).

A sequence located within the 30 kDa movement protein gene of the U1 strain of TMV serves as the origin of assembly. It is at this origin of assembly that the TMV RNA and the viral capsid protein spontaneously aggregate to initiate the assembly of virions (Butler, P. J. G., Mayo, M. A., Molecular architecture and assembly of tobacco mosaic virus particles, The molecular biology of the positive strand RNA viruses. (D. J. Rowlands, M. A. Mayo, and B. W. J. Mahy, eds.), Academic Press, London. pp. 237–257 (1987)). A functional origin of assembly is also required for efficient long distance movement (Saito, T., Yamanaka, K., and Okada, Y., *Virology* 176:329–336 (1990)). There does not appear to be any additional requirements for packaging. A variety of heterologous sequences can be encapsidated yielding rod-shaped virions whose lengths are proportional to the size of the RNA molecule containing the origin of assembly (Dawson, W. O. et al., *Virology* 172:285–292 (1989)).

Construction of plant RNA viruses for the introduction and expression of foreign genes in plants is demonstrated by French, R., et al., *Science* 231:1294–1297 (1986); Takamatsu, N., et al., *EMBO J* 6:307–311 (1987); Ahlquist, P., et al., *Viral Vectors,* Cold Spring Harbor Laboratory, New York, 183–189 (1988); Dawson, W. O., et al., *Phytopathology* 78:783–789 (1988); Dawson, W. O., et al., *Virology* 172:285–292 (1989); Cassidy, B., and Nelson, R., *Phytopathology* 80:1037 (1990); Joshi, R. L., et al., *EMBO J.* 9:2663–2669 (1990); Jupin, I., et al., *Virology* 178:273–280 (1990); Takamatsu, N., et al., *FEBS Letters* 269:73–76 (1990); Japanese Published Application No. 63-14693 (1988); European Patent Application No. 067,553; and European Patent Application No. 194,809, European Patent Application No. 278,667. Most of the viral vectors constructed in these references were not shown to be capable of systemic movement in whole plants. Rather, gene expression has only been confirmed in inoculated leaves. In other cases, systemic movement and expression of the foreign gene by the viral vector was accompanied by rapid loss of the foreign gene sequence (Dawson, W. O., et al., *Virology* 172:285 (1989)).

With further improvements, successful vectors have been developed based on tobamoviruses for rapid gene transfer to plants. (Donson et al., *Proc. Natl. Acad. Sci.* 88:7204–7208 (1991)). For example, the α-trichosanthin gene was added to the genome of a tobamovirus vector under the transcriptional control of a subgenomic promoter obtained from a strain distantly related to wild type TMV (Turpen, T. H., Ph.D. Dissertation, University of California, Riverside, pp. 72–87 (1992)). This vector is an autonomous virus, containing all known viral functions. Two weeks post-inoculation, transfected Nicotiana benthamiana plants accumulated α-trichosanthin to levels of at least 2% total soluble protein. Purified recombinant α-trichosanthin produced by this method was correctly processed and had the same specific activity as the enzyme derived from the native source. Therefore, messenger RNA produced by viral RNA amplification in whole plants is fully functional. However, after prolonged replication of certain sequences using this vector, some genetic instability was observed primarily due to recombinational deletions and point mutations (Kearney, C. M., et al., *Virology* (in press)).

Recently, very similar results were obtained using gene vectors derived from additional plus sense RNA viruses infecting plants; a potyvirus, tobacco etch virus ((Dolja, V., et al., *PNAS* 89:10208–10212 (1992) and a potexvirus, potato virus X (Chapman, S., et al., Plant Journal 2:549–557 (1992)).

Therefore, the major functional disadvantages of existing prior art viral vectors are their genetic instability regarding the fidelity of maintenance of some non-viral foreign genes in systemically infected whole plants, after prolonged replication and passaging. For many products, it will be desirable to increase the genetic fidelity by lowering the proportion of deletion and other variants in amplified populations.

An additional concern regarding the use of viral vectors for the expression of foreign genes in transgenic plants is biological containment of the viral vectors encoding for foreign genes.

SUMMARY OF THE INVENTION

The present invention relates to a replicon transcribed from a transgene integrated into the chromosome of a plant cell. The replicon encodes for replication origins possessing substantial sequence identity to a plus sense, single stranded RNA plant virus and at least one gene non-native to a plus sense, single stranded RNA plant virus. However, the replicon does not encode for at least one protein necessary for replication. According to the present invention, expression of the non-native gene is regulated by a helper virus encoding for a protein needed by the replicon for replication.

According to the present invention, it is preferred that the sequence encoding the non-native gene be located 5' to the 3' replication origin of the replicon. It is further preferred that the replicon encode for a gene needed by the helper virus for systemic infection, most preferably a viral movement protein located 3' to the 5' replication origin of the replicon.

The present invention also relates to a protein expressed in a plant cell using a replicon of the present invention. The present invention also relates to an RNA sequence expressed in a plant cell using the replicon of the present invention. The present invention also relates to a primary or secondary metabolite accumulated in the tissues of a transfected plant as a result of the expression of the non-native gene encoded by a replicon of the present invention. The present invention also relates to a transgenic plant comprising a transgene integrated into the chromosome of a plant cell wherein the transgene encodes for a replicon of the present invention.

The present invention also relates to a method of expressing a gene in a plant by integrating a transgene into a chromosome of a plant cell, the transgene encoding for a replicon of the present invention. The transgenic plant is then infected with a helper virus encoding for the protein needed by the replicon for replication.

BRIEF DESCRIPTION OF THE DRAWINGS

FIG. 6 provides a restriction map of the transgene portion of pBGC272.

Definitions

Foreign gene: A "foreign gene" refers to any sequence that is not native to the virus.

In cis: "In cis" indicates that two sequences are positioned on the same strand of RNA or DNA.

In trans: "In trans" indicates that two sequences are positioned on different strands of RNA or DNA.

Movement protein: A "movement protein" is a noncapsid protein required for cell to cell movement of replicons or viruses in plants.

Origin of Assembly: An "origin of assembly" is a sequence where self-assembly of the viral RNA and the viral capsid protein initiates to form virions.

Replication origin: A "replication origin" refers to the minimal terminal sequences in linear viruses that are necessary for viral replication.

Replicon: A "replicon" is an arrangement of RNA sequences generated by transcription of a transgene that is integrated into the host DNA that is capable of replication in the presence of a helper virus. A replicon may require sequences in addition to the replication origins for efficient replication and stability.

Transcription termination region: The "transcription termination region" is a sequence that controls formation of the 3' end of the transcript. Self-cleaving ribozymes and polyadenylation sequences are examples of transcription termination sequences.

Transgene: A "transgene" refers to the DNA sequence coding for the replicon that is inserted into the host DNA.

Virion: A "virion" is a particle composed of viral RNA and viral capsid protein.

DETAILED DESCRIPTION OF THE INVENTION

The instant invention provides high level expression of foreign genes in plants by viral replicons wherein the replicons possess improved genetic stability. The replicons of the instant invention are produced in host plant cells by transcription of integrated transgenes. The replicons of the instant invention are derived, in part, from single stranded plus sense plant RNA viruses.

Figure 2A:
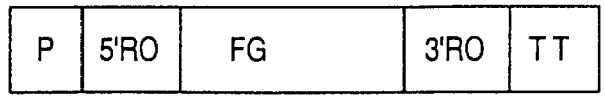
FIGS. 2A–2C depict the essential features of the instantly claimed viral replicons.
Figure 2B:
Figure 2C:
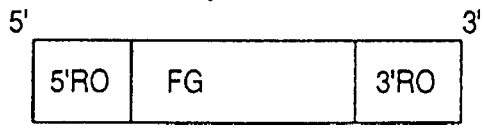

The replicons of the instant invention code for at least one foreign gene and possess sequences required in cis for replication ("replication origins"). FIG. 2(c). The replicons are produced by host cell transcription of a chromosomally integrated transgene to form an RNA transcript. The transgene is a DNA sequence that codes for the replicon and also contains a promoter and a transcription termination region. FIG. 2(a). The replicon is generated from an RNA transcript of the transgene by RNA processing and replication in the presence of a helper virus. FIG. 2(b).

The replicons of the instant invention lack functional replication protein sequences. Because the replicons of the instant invention lack replication protein sequences, they must rely on genetic complementation with helper viruses for replication. The replicon's dependency on the helper virus for replication enables regulatable amplification of these replicons through the introduction of the helper virus.

Genetic complementation of the replicon with a helper virus provides many advantages over autonomous viral vectors for amplifying gene expression. Each infected cell of a transgenic plant contains a correct master copy of the gene to be amplified. This reduces the effects of genetic drift in replicating RNA populations that can result in sequence instabilities and point mutations after prolonged replication of an RNA vector (Kearney, C. M., et al., *Virology* (in press)).

Figure 3:
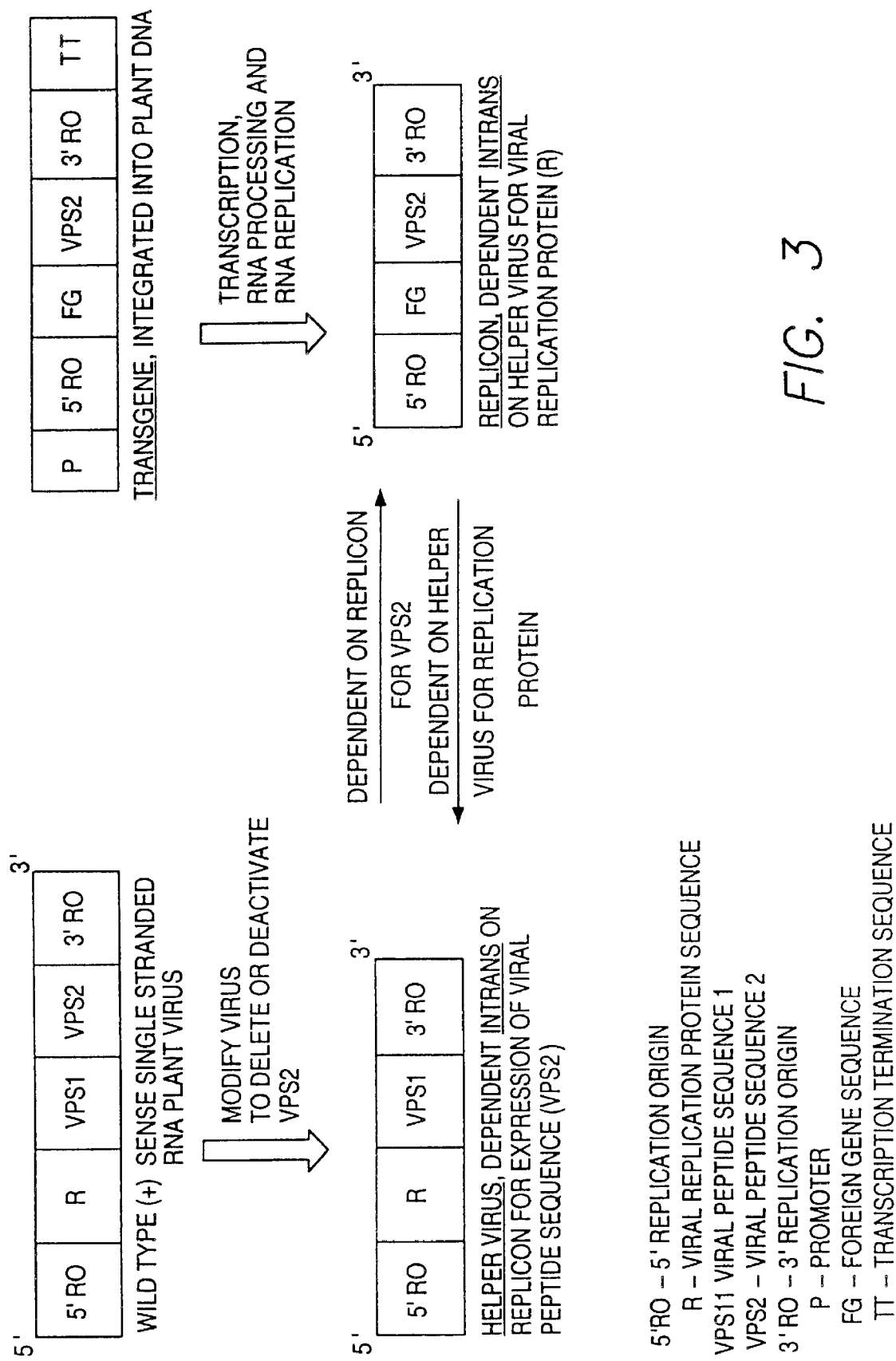
FIG. 3 depicts an embodiment where the replicon and helper virus are mutually dependent.

In a further embodiment of the instant invention, the replicon codes for at least one sequence upon which the helper virus is dependent. Thus, in this further embodiment, the replicon and the helper virus are mutually dependent. [See FIG. 3]. Helper virus dependence on the replicon insures amplified expression of the replicon sequences by the helper virus in whole plants.

In a further embodiment, the replicon codes for a functional movement protein such as the 30 kDa TMV movement protein. The helper virus used in this embodiment does not possess a functional movement protein. Thus, the helper virus is dependent on the replicon for movement functionality. Movement proteins are necessary for cell to cell movement in plants. By placing a functional movement protein sequence on the replicon and either deactivating or deleting the same sequence on the helper virus or by using a host species with helper virus encoded movement protein incompatibility, the helper virus's dependency on the replicon enables systemic infection of the whole plant with the viral replicon plus helper virus.

This embodiment of the instant invention has the further advantage that the only virus released into the environment will be a debilitated helper virus. Thus, the helper virus will not be able to spread in plants that do not already contain a functional copy of the viral movement protein. This embodiment provides an option for more stringent levels of biological containment which may be desirable in some cases for large scale commercial production.

Figure 4:
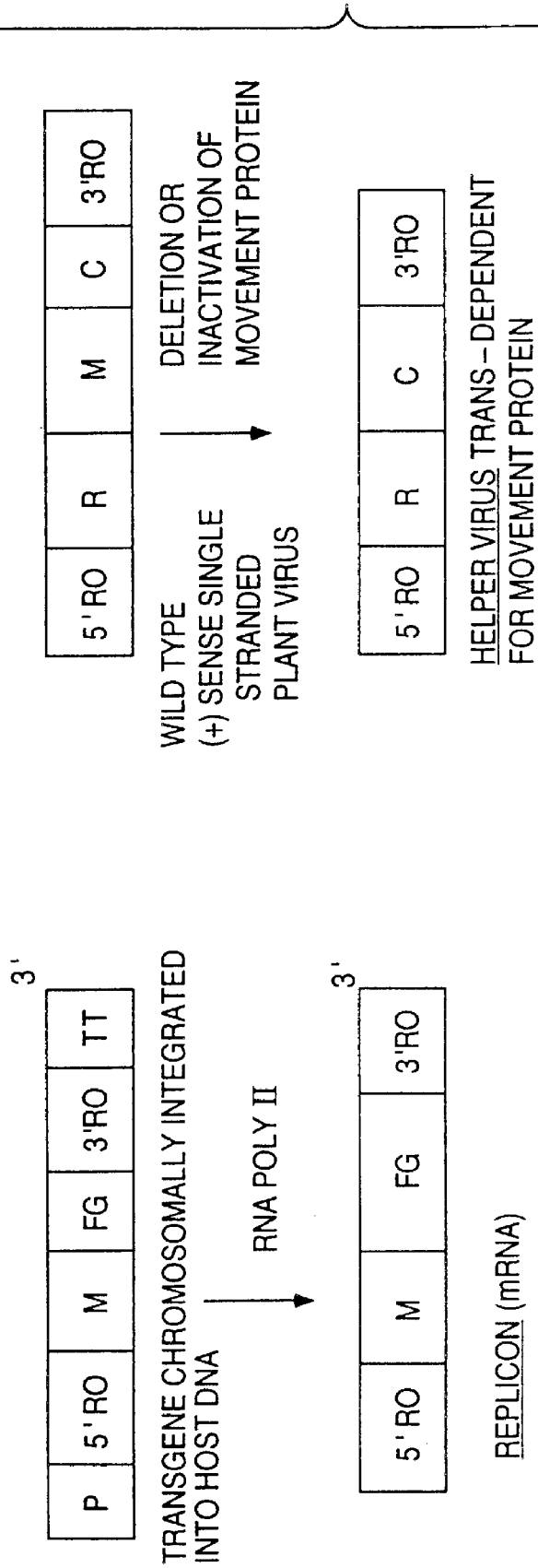
FIG. 4 depicts a preferred replicon gene arrangement where the foreign gene is situated at the 3' end of the genome 5' to the 3' replication origin.

In a preferred embodiment, the replicon is formulated such that the sequences encoding the replication origins and the movement functions are linked to the foreign gene sequences. The chromosomally integrated transgene that codes for the replicon is transcribed by host RNA polymerase II producing recombinant mRNAs. In the presence of a helper virus, these transcripts are replicated as additional replicon components in a mixed population. During viral replication, subgenomic messenger RNA may be produced from replicon RNA resulting in amplified expression of foreign genes. The most preferred replicon gene arrangement places the foreign gene at the extreme 3' end of the genome where the viral structural protein is normally encoded. See FIG. 4. This position for the foreign gene at the extreme 3' end of the genome, as depicted in FIG. 4, is critical for high level expression (Culver, J. N., et al., *Virology* (in press)). However, the protein coding sequences or other gene sequences located between the replication origins may be functional in any order.

Additional preferred embodiments of the replicon sequence include the use of regulatable promoters to control expression of the foreign gene and/or movement protein. One promoter for expression of a fusion protein containing the foreign protein or a series of subgenomic promoters may be employed. Self-cleaving ribozymes or a polyadenylation region may also be employed as the transcription termination regions.

The replicons are generated in vivo in plants through transcription of transgenes that are integrated into the host plant cell chromosome and through replication in the presence of a helper virus. The transgenes can be introduced into the host plant cell chromosome by known transformation methods using a variety of promoters. After the replicon has been introduced into the host, the resulting transgenic plants are grown to an optimized stage at which point a helper virus strain is added. The replicons are then amplified by the introduced helper virus and the foreign gene is expressed.

The foreign gene product coded for and expressed by the replicon can be a very wide variety of RNA or proteins products and include, for example, antisense and ribozyme RNA, regulatory enzymes, and structural, regulatory and therapeutic proteins that may be expressed in their native form or as gene fusions. Typical therapeutic proteins include members of the interleukin family of proteins and colony stimulating factors such as CSF-G, CSF-GM and CSF-M. It is understood, however, that any therapeutic protein can be coded for and expressed in the instant invention.

If expression of the foreign gene results in the accumulation of a protein or other material in the plant tissues, that resulting product may be harvested once the desired concentration of that product is achieved. Significant quantities of recombinant proteins, nucleic acids or other metabolites can be inexpensively produced using this procedure. The low level of expression and wide variation that is observed in transgenic organisms chromosomally transformed with the same construct (a phenomenon attributed to "position effects"), is avoided by this method. RNA-based amplification is not critically dependent on initial transcript amounts. There is also no theoretical limit to the number of genes that can be amplified at the RNA level. The target gene remains "off" before amplification because subgenomic mRNA is only produced during viral replication. Therefore this approach might be particularly appropriate for controlling complex biochemical pathways or producing products that are toxic to the plant. It would be feasible for example, to overexpress critical enzymes in a pathway and simultaneously down-regulate other genes by amplifying antisense RNA only after inoculation with a helper virus. These types of manipulations are not possible using existing or proposed technologies for chromosomal transformation of plants or plant cell cultures or by using prior art viral vectors.

DESCRIPTION OF THE PREFERRED EMBODIMENTS

The following examples further illustrate the present invention.

EXAMPLE 1

Construction of a Transgene for Expression of Recombinant Messenger RNA

Figure 1:
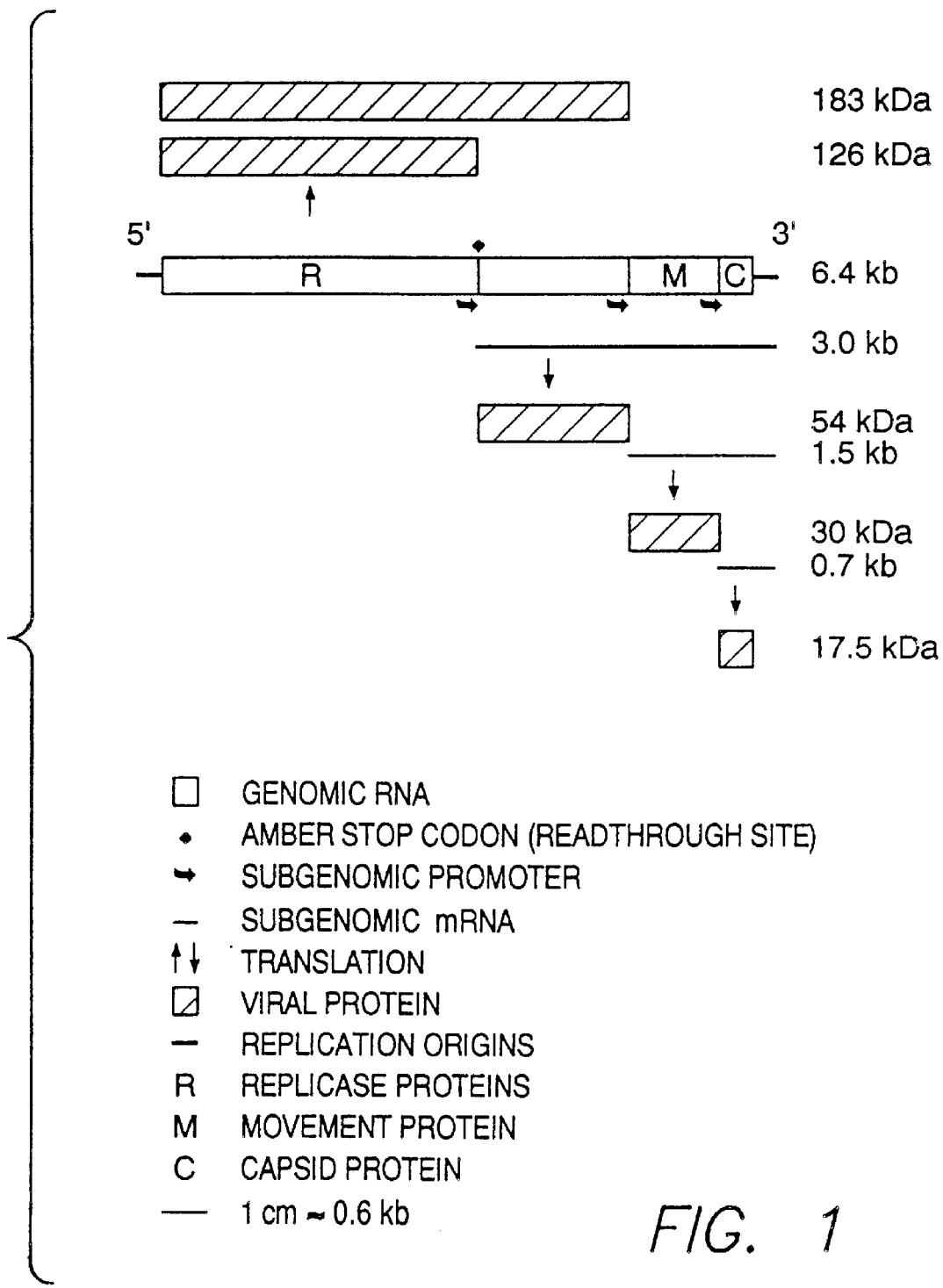
FIG. 1 depicts the genome of wild type TMV.

Construction of a transgene derived from TMV is set forth herein. The wild type TMV genome is set forth in FIG. 1. The construction of DNA plasmids containing the 5' replication origin fused to the CaMV 35S promoter are described in (Ow, D. W., et al., *Science* 234:856–859 (1986)) and the 3' replication origin fused to a ribozyme termination region are described by Turpen, T. H., Ph.D. Disertation, University of California, Riverside, pp. 88–105 (1992).

The substitution of the coat protein gene for the coding sequence of CAT is described in Dawson, et al., *Phytopathol.* 78:783–789 (1988).

Figure 5:
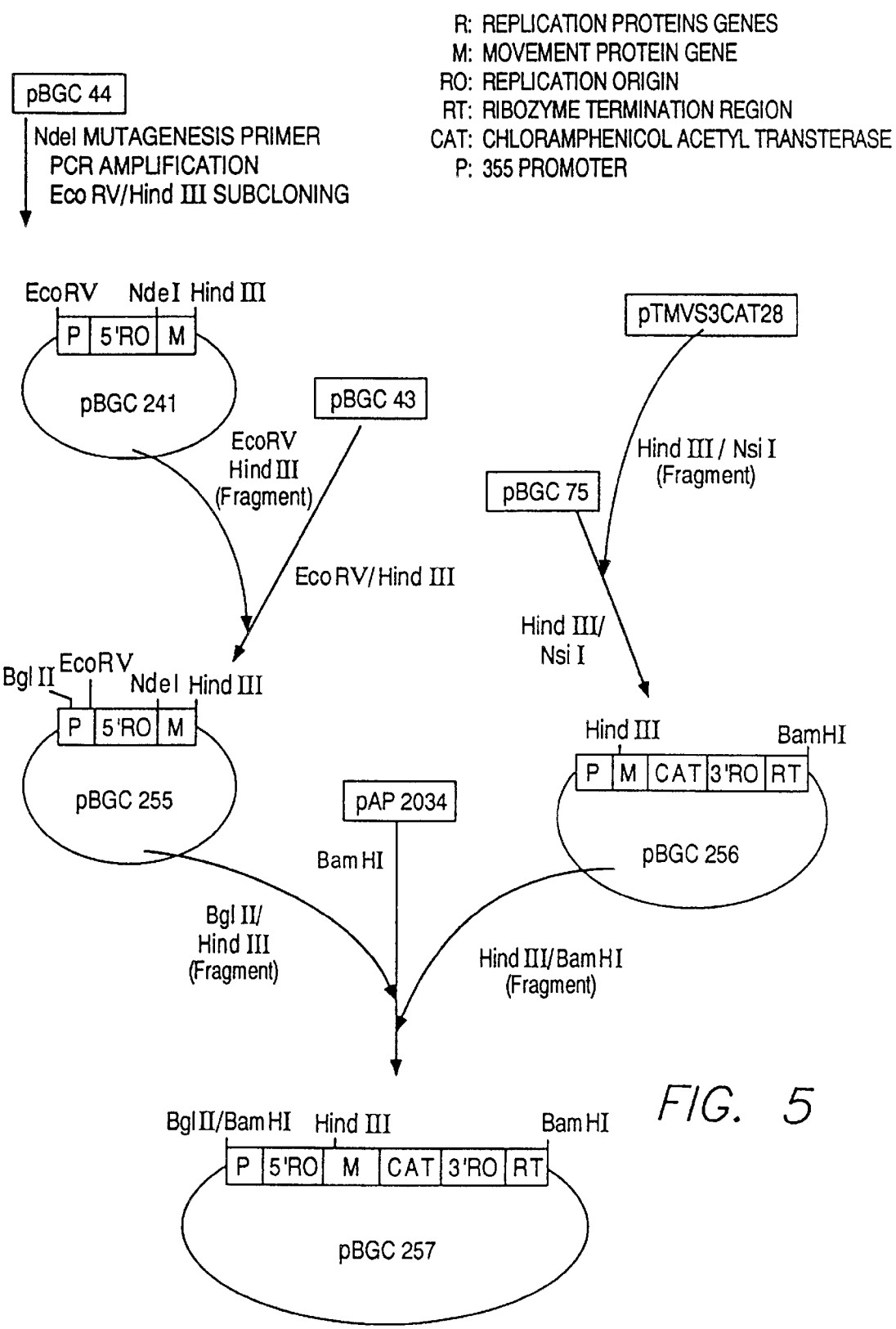
FIG. 5 depicts the construction of a transgene for the synthesis of a replicon encoding Chloramphenicol Acetyltransferase (CAT) in an Agrobacterium transformation vector.

Previously disclosed plasmids, pBGC43, pBGC44, pBGC75 (Turpen, T. H., Ph.D. Disertation, University of California, Riverside, pp. 88–136 (1992)) and pTMVS3CAT28 (Dawson, et al., *Phytopathol.* 78:783–789 (1988)) are used as precursors for the construction of the desired transgene for synthesis of replicon RNA (FIG. 5). Construction of plasmids pBGC43, pBGC44, pBGC75 are described in Table 1 taken from Turpen, T. H., Ph.D. Disertation, University of California, Riverside, pp. 92, 112 (1992). Construction of plasmids pBGC43, pBGC44, pBGC75 and pTMVS3CAT28 are also discussed below.

Preparation of pTMVS3-CAT-28 pTMVS3-CAT-28 containing a substitution of the chloramphenicol acetlytransferase (CAT) gene for the coat protein gene was constructed as follows. The CAT gene was removed from pCM1 (Pharmacia) with SalI and ligated into XhoI-cleaved pTMVS3-28. pTMVS3-28 was constructed by cloning genomic length TMV CDNA (6.4 kb) in pBR322 as described in Dawson W., et al., *Proc. Natl. Acad. Sci.* 83:1832–36, (1986). The CAT construction produced pTMVS3-CAT-28 from which the mutant cp S3-CAT-28 was transcribed. Correct sequence and orientation were confirmed by sequencing. *Gene Anal. Technol.* 2:89–94.

Preparation of pBGC43 pTK49 was constructed by cloning the 1.4 kb PstI-HindIII fragment of TMV cDNA in pUC19 as described by Dawson, W., et al., *Proc. Natl. Acad. Sci.* 83:1832–36 (1986). The 1.4 kb PstI-HindIII from pTK49 was recloned into pUC19 to form pTT1. The 1.6 kb HindIII-BamHI fragment from pDO432 described in Ow et al., *Science* 234:856–59, (1986) was cloned into pTT1. NotI linkers were added at the HindIII site of the fragment and the EcoRI site of the vector. pTT3 was constructed by digesting pTT2 with PstI-BamHI and mung bean nuclease to position the 35S promoter at the 5' end of TMV cDNA. The 1.9 kb NotI-SmaI fragment of pTT3 was cloned into pBStKs+ to form pBGC43.

Preparation of DBGC44

The 1.4 kb SalI-HindIII fragment from pTT1 was cloned into pstSk- to form pBGC8. The 3.6 kb HindIII fragment from pTMV204 disclosed in Dawson, et al., *Proc. Natl. Acad. Sci.* 83:1832–36, (1986) was cloned into pBGC8 to form pBGC9. The 4.8 kb SmaI-PstI fragment from pBGC9 was cloned into pBGC43 (described above) to form pBGC44.

Preparation of pBGC 75

The 2.1 kb EcoRI-PstI fragment from pTMV204 described in Dawson, W., et al., *Proc. Natl. Acad. Sci.* 83:1832–36, (1986) was cloned into pBstSk- to form pBGCll. The 3.6 HindIII fragment from pTMV204 was cloned into pBGCll to form pBGC14. The 0.4 kb NcoI-PstI fragment of pTMVcpS3-28 (0.5 kb coat protein deletion of pTMV304, described in Dawson, W., et al. *Phytopathology* 78:783–789) was substituted for the 0.9 kb NcoI-PstI fragment of pGC14 to form pGC15. pBGC19 was formed by deleting the 0.03 kb KpnI-HindIII polylinker region of pBGC14.

pBGC70 was formed by cloning a 0.05 kb synthetic ApaI-PstI ribozyme encoding fragment into pBstSk+. pBGC72 was formed by deleting the 3.5 kb ClaI fragment from pBGC19. pBGC73 was formed by cloning the 0.05 kb ApaI-PstI fragment of pBGC70 into pBGC72. pBGC74 was formed by substituting the 0.1 kb ClaI-NsiI fragment of pBGC15 for the 0.5 kb ClaI-NsiI fragment of pBGC73. The 3.5 kb ClaI fragment of pBGC19 was cloned into pBGC74 to form pBGC75.

TABLE 1

| Designation | Relevant Characteristics | Source or Reference |
|---|---|---|
| *E. coli* | | |
| JM109 | recA1, endA1, gyrA96, thi-, hsdR17($r_{K-}$, $m_{K+}$), supE44, relA1, Δ(kac-proAB), [F traD36, proAB, lacI$^q$ZΔM15] | Yanish-Perron et al. Gene 33:103–199 (1985) |
| HB101 | hsdS20 ($r_{B-}$, $m_{B-}$), supE44, ara14, gelK2, lecY1, proA2, rspL20, xyl-5, mtl-1 recA13 | Sambrook et al. Molecular Cloning: A Laboratory Manual Cold Spring Harbor Laboratory (1989) |
| GJ23 | General plasmid mobilizing strain containing pGJ28 and pR64drd11 | Van Haute et al. EMBO J. 2:411–417 (1983) |
| *A. tumefaciens* | | |
| C58C1 | Rif$^r$ derivative of strain C58 containing pGV3850 | Zambryski et al. EMBO J. 2:2143–2150 (1983) |
| A. t.-17 | TMV transfection strain containing pGV3850::pBGC17 | Turpen, T. H., Ph.D. Dissertation, University of California, Riverside, pp. 106–132 (1992) |
| A. t.-46 | TMV transfection strain containing pGV3850::pBGC46 | Turpen, T. H., Ph.D. Dissertation, University of California, Riverside, pp. 106–132 (1992) |
| A. t.-49 | TMV transfection strain containing pGV3850::pBGC49 | Turpen, T. H., Ph.D. Dissertation, University of California, Riverside, pp. 106–132 (1992) |
| A. t.-77 | TMV transfection strain containing pGV3850::pBGC77 | Turpen, T. H., Ph.D. Dissertation, University of California, Riverside, pp. 88–105 (1992) |
| Plasmids | | |
| pBstSK/ pBstKS | *E. coli* cloning plasmids, pBluescript (+/−) | Stratagene, La Jolla, California |
| pUC18/pUC19 | *E. coli* cloning plasmids | Yanish-Perron et al. Gene 33:103–199 (1985) |
| pT7/T3α19 | *E. coli* cloning plasmid | BRL, Gaithersburg, MD |
| pTK49 | 1.4 kb PstI-HindIII fragment of TMV cDNA in pUC19 | Dawson et al. Proc. Natl. Acad. Sci. U.S.A. 83:1832–1836 (1986) |
| pTMV204 | Genomic length TMV cDNA (6.4 kb) in pBR322 | Dawson, et al. Proc. Natl. Acad. Sci. U.S.A. 83:1832–1836 (1986) |
| pTMV212 | Genomic length TMV cDNA in pT7/T3α19 | Dawson, unpublished |
| pTMVcpS3-28 | Coat protein deletion (0.5 kb) mutant of pTMV204 | Dawson et al. Phytopathology 78:783–789 (1988) |
| pAP2034 | pBR322-___sed selection-expression vector for plant transformation, Cb$^r$, Sp$^r$, Kn$^r$ | Velton et al. Nucleic Acids Res. 13:6981–6998 (1985) |
| pDO432 | Source of restriction site modified 35S promoter | Ow et al. Science 234:856–859 (1986) |
| pTT1 | 1.4 kb PstI-HindIII fragment from pTK49 cloned in pUC19 | Turpen, T. H., Ph.D. Dissertation, University of California, Riverside, pp. 106–132 (1992) |
| pTT2 | 1.6 kb HindIII-bamHI fragment from pDO432 cloned in pTT1, NotI linkers added at KindIII site of fragment and EcoRI site of vector | Turpen, T. H., Ph.D. Dissertation, University of California, Riverside, pp. 106–132 (1992) |
| pTT3 | PstI-BamHI + mung bean nuclease deletion of PTT2 positioning 35S promoter at 5'-end of TMV cDNA | Turpen, T. H., Ph.D. Dissertation, University of California, Riverside, pp. 106–132 (1992) |
| pBGC6 | 0.2 kb XhoI-PstI fragment from pTMVcpS3-28 in pBstKS+ | Turpen, T. H., Ph.D. Dissertation, University of California, Riverside, pp. 106–132 (1992) |
| pBGC8 | 1.4 kb SalI-HindIII fragment from PTT1 cloned in pBstSK− | Turpen, T. H., Ph.D. Dissertation, University of California, Riverside, pp. 106–132 (1992) |
| pBGC9 | 3.6 kb HindIII fragment from pTMV204 cloned in pBGC8 | Turpen, T. H., Ph.D. Dissertation, University of California, Riverside, pp. 106–132 (1992) |
| pBGC11 | 2.1 kb EcoRI-PstI fragment from pTMV204 cloned in pBstSK− | Turpen, T. H., Ph.D. Dissertation, University of California, Riverside, pp. 106–132 (1992) |
| pBGC14 | 3.6 kb HindIII fragment from pTMV204 cloned in pBGC11 | Turpen, T. H., Ph.D. Dissertation, University of California, Riverside, pp. 106–132 (1992) |
| pBGC15 | 0.4 kb NcoI-PstI of pTMVcpS3-28 substituted for 0.9 kb NcoI-PstI fragment of pBGC14 | Turpen, T. H., Ph.D. Dissertation, University of California, Riverside, pp. 88–105 (1992) |
| pBGC16 | 3.3 kb SalI-BamHI fragment of pBGC9 cloned in pAP2034 | Turpen, T. H., Ph.D. Dissertation, University of California, Riverside, pp. 106–132 (1992) |
| pBGC17 | Full length wtTMV cDNA in pAP2O34 | Turpen, T. H., Ph.D. Dissertation, University of California, Riverside, pp. 106–132 (1992) |

TABLE 1-continued

| Designation | Relevant Characteristics | Source or Reference |
|---|---|---|
| pBGC19 | 0.03 kb KpnI-HindIII polylinker deletion of pBGCT4 | Turpen, T. H., Ph.D. Dissertation, University of California, Riverside, pp. 106–132 (1992) |
| pBGC43 | 1.9 kb NotI-SmaI fragment from pTT3 cloned in pBstKS+ | Turpen, T. H., Ph.D. Dissertation, University of California, Riverside, pp. 106–132 (1992) |
| pBGC44 | 4.8 kb SmaI-PstI fragment of pBGC9 cloned in pBGC43 | Turpen, T. H., Ph.D. Dissertation, University of California, Riverside, pp. 106–132 (1992) |
| pBGC45 | 4.3 kb BglII-BamHI fragment of pBGC44 cloned in the BamHI site of pAP2034 | Turpen, T. H., Ph.D. Dissertation, University of California, Riverside, pp. 106–132 (1992) |
| pBGC46 | 3.1 kb BamHI fragment of pBGC44 cloned in the BamHI site of pAP2043 | Turpen, T. H., Ph.D. Dissertation, University of California, Riverside, pp. 106–132 (1992) |
| pBGC49 | 2.6 kb BamHI fragment of pBGC14 cloned in the BamHI site of pBGC45 | Turpen, T. H., Ph.D. Dissertation, University of California, Riverside, pp. 106–132 (1992) |
| pBGC70 | 0.05 kb synthetic ApaI-PstI ribozyme encoding fragment cloned in pBstSK+ | Turpen, T. H., Ph.D. Dissertation, University of California, Riverside, pp. 88–105 (1992) |
| pBGC72 | 3.5 kb ClaI deletion of pBGC19 | Turpen, T. H., Ph.D. Dissertation, University of California, Riverside, pp. 88–105 (1992) |
| pBGC73 | 0.05 kb ApaI-PstL fragment of pBGC70 cloned in pBGC72 | Turpen, T. H., Ph.D. Dissertation, University of California, Riverside, pp. 88–105 (1992) |
| pBGC74 | 0.1 kb ClaI-Nsil fragment of pBGC15 substituted for for 0.5 kb ClaI-Nsil gragment of pBGC73 | Turpen, T. H., Ph.D. Dissertation, University of California, Riverside, pp. 88–105 (1992) |
| pBGC75 | 3.5 kb ClaI fragment of pBGC19 cloned into pBGC74 | Turpen, T. H., Ph.D. Dissertation, University of California, Riverside, pp. 88–105 (1992) |
| pBGC77 | 2.7 kb BamHI fragment of pBGC75 cloned into pBGC45, 35S promoter plus full length cp-TMV cDNA in pAP2034 with rebozyme self-cleaving fragment at 3'-terminus | Turpen, T. H., Ph.D. Dissertation, University of California, Riverside, pp. 88–105 (1992) |

With regard to construction of the transgene, it is desired to place the 30-kDA movement protein gene at precisely the same position as the replicase gene (relative to 5' replication origin in the wild type TMV genome, See FIG. 5). To accomplish this, a NdeI site is introduced at the start codon of each gene by PCR-based mutagenesis using synthetic primers and unique adjacent cloning sites. A 270 bp mutagenesis product containing the internal NdeI site from the PCR primer is subcloned using the EcoRV site in the cauliflower mosaic virus 35S promoter and the HindIII site in the 30-kDa protein gene. The ligation product is then sequence verified.

The 3' segment of the replicon, containing the CAT gene will be placed adjacent to the 3'-ribozyme as a HindIII-NsiI fragment from the transient TMV vector pTMVS3CAT28 (FIG. 5). In the final cloning step, the 5' portion of the transgene and the 3' portion will be subcloned into the unique BamHI site of the plant transformation vector pAP2034 (Velton and Schell, *NAR 13:6981–6998* (1985) as a BglII-BamHI fragment described previously (Turpen, T. H., Ph.D. Disertation, University of California, Riverside, pp. 88–132 (1992)). The sequence of the replicon RNA, produced by host transcription, RNA processing, and replication in the presence of a helper virus is given as SEQ. No. 1. Thus, the foreign gene (CAT) is placed on a RNA viral replicon, under control of the coat protein subgenomic promoter for messenger RNA synthesis (located at the 3' end of the movement protein gene).

EXAMPLE 2

Transformation of Plants

In one embodiment of this invention, *Agrobacterium tumefaciens* is used for insertion of this sequence into the plant chromosome as described previously (Turpen, T. H., Ph.D. Dissertation, University of California, Riverside, pp. 106–132 (1992)). The transformation vector pAP2034 is a cointegrating type Agrobacterium vector. pAP2034 containing the transcription unit for the production of replicon RNA is mobilized into *A. tumefaciens* by conjugation using the helper strain GJ23 (Van Haute, E., Joos, et al., *EMBO J.* 2:411–417 (1983)). Transconjugants are selected and the structure of the cointegrate between donor plasmid and the disarmed Ti plasmid pGV3850 (Zambryski, P., et al., *EMBO J.* 2:2143–2150 (1983)) is confirmed by Southern blot hybridization. A correct homologous recombination event places the transgene construct between the T-DNA borders.

Axenic leaf segments of *N. tabacum* cv. Xanthi are treated (Horsch, R.B., et al., Leaf disc transformation, *Plant molecular biology manual.* (S. B. Gelvin, R. A. Schilperoort, and D. P. S. Verma, eds.), Kluwer Academic Publishers, Dordrecht, The Netherlands, pp. A5:1–9 (1988)) in the following sequence: day 1; leaf segments are dipped in *A. tumefaciens* liquid culture and placed on regeneration media (RM), day 3; explants are transferred to RM supplemented with cefotaxime (500 $\mu$g/ml), day 5; explants are transferred to RM/cefotaxime (500 $\mu$g/ml)+kanamycin (100 $\mu$g/ml), day 30–40; shoots excised and placed onto rooting media containing cefotaxime (500 $\mu$g/ml) and kanamycin (100 $\mu$g/ml). Cultures are maintained under continuous fluorescent light (Sylvania GTE, Gro-Lux WS) at 20° C.

Hardened plants are grown in commercial potting soil (Cascade Forest Products Inc., Arcata, Calif.) at a temperature of 21°–29° C., with a controlled release fertilizer (Osmocote, 14-14-14) using natural light (Vacaville, Calif.) supplemented with fluorescent light on a 16 hr day length in an indoor greenhouse. The antibiotic resistance trait carried in transgenic lines is scored by germinating seedlings in sterile agar in the presence of 100 ug/ml kanamycin (Dunsmuir, P., et al., Stability of introduced genes and stability of expression, *Plant molecular biology manual.* (S. B. Gelvin, R. A. Schilperoort, and D. P. S. Verma, eds.), Kluwer Academic Publishers, Dordrecht, The Netherlands, pp. C1:1–17 (1988)).

EXAMPLE 3

Production of Replicon RNA in the Presence of Helper Virus

The sequence of the replicon RNA, produced by host transcription, RNA processing, and replication in the presence of a helper virus, is given as SEQ. No. 1. Tobamoviruses with mutations or naturally occurring variation in the 30-kDa protein gene are deficient in cell-to-cell movement on specific host species. Transgenic plants or alternate hosts can complement this defect. It will be appreciated to those skilled in the art that there are numerous methods of producing helper tobamoviruses by genetic engineering or by mutagenesis in addition to those helper variants or host species combinations occurring naturally. Likewise, methods for producing transgenic plants which express 30 kDa protein and which complement defective 30 kDa containing viruses have been published. For example, movement deficient helper viruses can be synthesized by transcription of TMV with known mutations for the production of RNA inoculum. Transgenic plants expressing the 30-kDa protein complement this defect (Deom, C. M., et al., *Science* 237:389–394 (1987)). Therefore, large quantities of a helper virus can be propagated. In one embodiment of this invention, a 30-kDa protein frameshift mutant, having a single base pair deletion at position 4931 thereby creating a EcoRV site in the cDNA, is used as helper virus. Transgenic tobacco (~100 plants) are regenerated containing this replicon transgene construction and assayed for CAT activity in the presence and absence of helper viruses using procedures described (Shaw, W. V., Chloramphenicol acetyltransferase from chloramphenicol-resistant bacteria, *Methods in Enzymology*, Vol. 53, (S. Fleischer and L. Packer, eds.), pp. 737–755 (1975)). 200 mg of leaf tissue is macerated in assay buffer followed by the addition of 0.5 mM acetyl CoA and 0.1 uCi [$^{14}$C]chloramphenicol, incubation for 45 min at 37° C., extraction, resolution by thin-layer chromatography, and autoradiography.

EXAMPLE 4

Production of CAT in Tobacco Plants Using a Replicon RNA in the Presence of Helper Virus Several tobacco plants (*Nicotiana tabacum*) were transformed with a transgene of the present invention in order to evaluate the ability of the transgene to be expressed within a plant cell as well as the ability of the transgene to systemically infect a plant and express a protein encoded by the transgene. In the present example, systemic expression of chloramphenicol acetyl transferase encoded by the transgene was achieved at a level two fold that of the background level and comparable to levels obtained for single copy tobacco genes.

In the present example, pBGC272 and pBGC273 were used to introduce the transgenes. A restriction map of the transgene portion of pBGC272 is provided in FIG. 6. pBGC272 has been deposited with the American Type Culture Collection, Rockville, Md. (ATCC) under Accession No. 75632. It is predicted that amplified expression of CAT from pBGC272 would be observed in the presence of a helper virus through complementation with the helper virus.

A control plasmid, pBGC273, was also prepared which differs from pBGC272 in that the 3' noncoding region has been deleted. Amplified expression of CAT is not expected with pBGC273 because deletion of the 3' noncoding region prevents synthesis of the minus strand.

Identification of Transcript Production

Tobacco plants were transformed with either pBGC272 or pBGC273 using the *Agrobacterium tumefaciens* leaf-dip method as described in Example 2. In order to save time, bacterial conjugation was avoided by using a binary plasmid vector system for plant transformation instead of employing cointegrate vectors. Bevan, M., et al. *Nucleic Acid Res.* 12:8711–8721 (1984).

Figure 7:
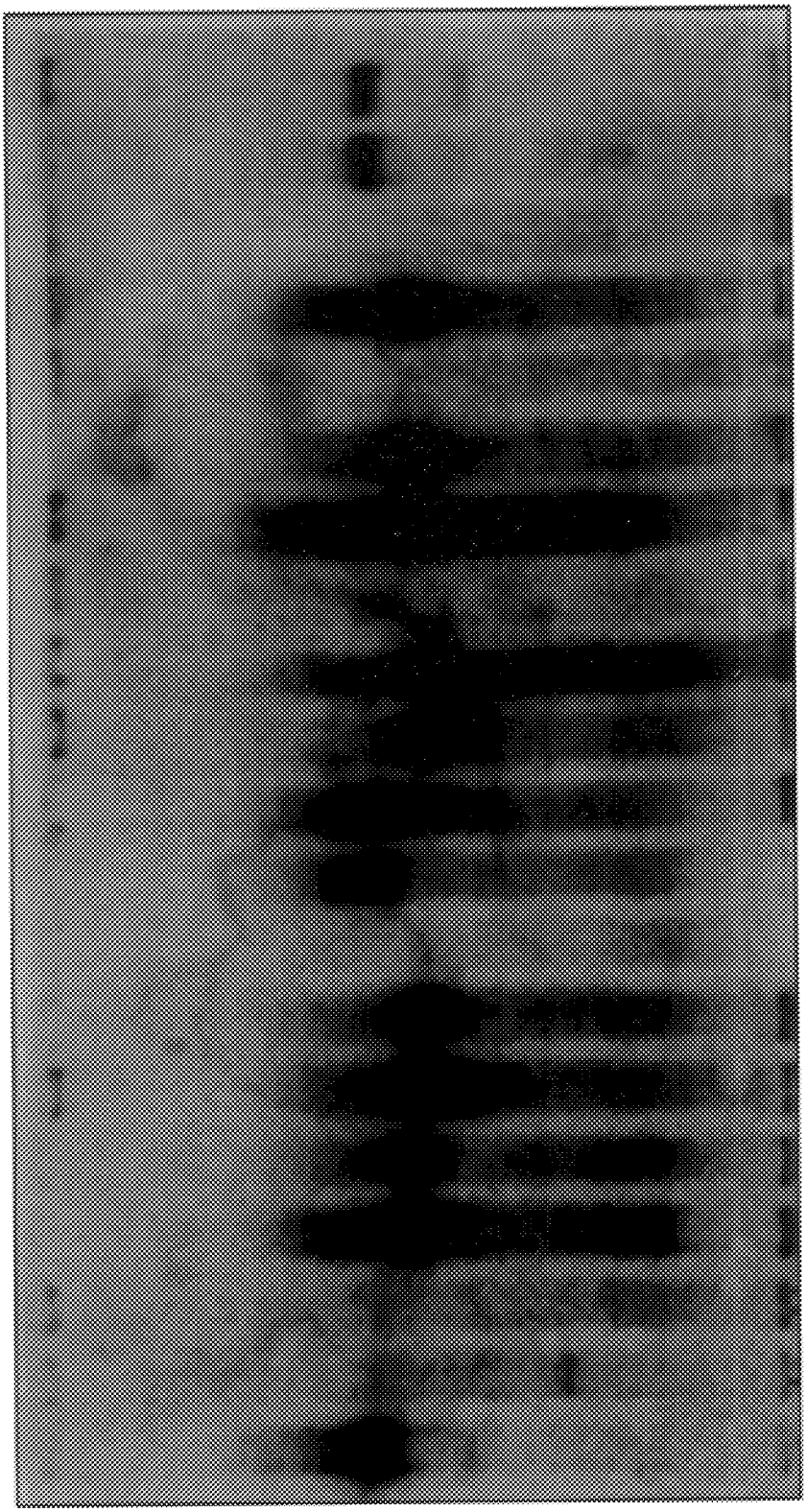
FIG. 7 depicts an autoradiograph showing the separation and identification of pBGC272 and pBGC273.

The presence of the viral transcripts after inoculation was measured by northern hybridization. Specifically, total RNA was purified, glyoxalated, separated by electrophoresis, blotted to a nylon membrane (Nytran) and probed with the NdeI-NsiI fragment of pBGC272 which had been $^{32}$P-labeled by the random primer method. An autoradiograph showing the separation and identification of pBGC272 and pBGC273 is depicted in FIG. 7. Lanes 1, 2 and 20 contain control DNA restriction fragments from pBGC272. Lanes 3–10 and 13–18 contain total RNA from transgenic plant samples (pBGC272, pBGC273). Lanes 11 and 12 contain control samples from 30K transgenic plants (line 26C) known to complement helper virus TMMVDEcoRV. Lane 19 contains RNA (1/220 equivalent) from helper virus TMMVDEcoRV-infected line 26C control plants.

Out of 16 plants transformed with pBGC272, 12 contained abundant levels of transcript. Similarly, out of 6 plants transformed with pBGC273, 4 plants produced transcripts.

Identification of CAT Production

The ability of pBGC272 to systemically infect a plant and produce a marker protein, chloramphenicol acetyl transferase (CAT), was also evaluated. CAT concentrations were determined using an ELISA assay. Gendloff, E., et al. *Plant Mol. Biol.* 14:575–583 (1990). Leaf disc samples (#8 core bore) were used. Total soluble protein from the same leaf disk samples used for CAT/ELISA was determined by the method Bradford, M. *Anal. Biochem.* 72:248–254 (1976).

Three groups of plants containing pBGC272 or pBGC273 by the *Agrobacterium tumefaciens* leaf-dip method were infected with one of three helper viruses. The helper viruses used in the present example include the wild type TMV virus (TMVU1), TMVDEcoRV and TMV3OK-O. The helper viruses used in the present study are derived from the readily available tobamovirus strains, TMVU1 (also known as the common or wild type strain, ATCC No. PV 135) and odonoglossum ringspot tobamovirus (ORSV, ATCC No. PV274). Paul, H., C.M.I./A.A.B. Descriptions of Plant Viruses, No. 155 (TMVU1); Zaitlin, M., C.M.I./A.A.B. Descriptions of Plant Viruses, No. 151 (ORSV).

Helper virus TMVDEcoRV contains a point mutation in the TMV 30K gene. TMVDEcoRV was created by deleting nucleotide 4931 by oligonucleotide site directed mutagenesis of TMVU1 cDNA, thereby introducing an EcoRV site at this position and causing a frame shift mutation in the 30K gene. Infectious RNA transcripts are then synthesized in vitro and used as inoculum.

TMV30K-O contains the 30K gene from odonoglossum ringspot tobamovirus (ORSV) in a U1 strain background. TMV30K-O is partially deficient in movement function, showing delated and sporadic systemic infection in *Xanthi tobacco*. Dawson, W., et al. *Ann. Rev. Plant Physiol. Plant Mol. Biol.* 43:527–555 (1992). Helper virus TMV30K-O may be prepared by substituting the cDNA encoding the 30K gene of the TMVU1 strain with the 30K gene from ORSV by routine genetic manipulation techniques. Infectious RNA transcripts are then synthesized in vitro and used as inoculum.

The first group of plants (147 individuals) were infected with TMVDEcoRV. Plants containing pBGC272 did not show symptoms of systemic infection and were thus unable to complement the helper virus or amplify CAT expression.

The second group of plants (9 individuals) were infected with TMVU1. These plants exhibited systemic infection of the wild type virus but were unable to amplify CAT expression above background control levels because genetic complementation is not necessary for systemic infection of the plant with a wild type helper virus.

The third group of plants (78 individuals) were infected with TMV30K-O. Of the 78 inoculated plants, 24 individuals became systemically infected earlier than plants inoculated solely with TMV30K, indicating complementation of the movement function debilitated helper virus with pBGC272.

Of the 24 systemically transformed plants, 19 plants had been infected with pBGC272 and 5 with pBGC273. Of the 19 plants transformed with pBGC272, 12 were found to contain elevated levels of CAT. Upon resampling and assaying in triplicate, 8 plants were found to have CAT levels of roughly 0.1 ng CAT/mg of total soluble protein which is two fold that of the background level.

Biological Deposits

The following plasmids have been deposited at the American Type Culture Collection (ATCC), Rockville, Md., U.S.A., under the terms of the Budapest Treaty on the International Recognition of the Deposit of Microorganisms for the Purposes of Patent Procedure and Regulations thereunder (Budapest Treaty) and are thus maintained and made available according to the terms of the Budapest Treaty. Availability of such plasmids is not to be construed as a license to practice the invention in contravention of the rights granted under the authority of any government in accordance with its patent laws.

The deposited cultures have been assigned the indicated ATCC deposit numbers:

| Plasmid | ATCC No. |
|---------|----------|
| pBGC272 | 75632    |

Pursuant to 37 C.F.R. §1.808, applicants agree that all restrictions imposed by the depositor on the availability to the public of the deposited plasmids will be irrevocably removed upon the granting of a patent on the present application.

While the invention of this patent application is disclosed by reference to the details of preferred embodiments of the invention, it is to be understood that this disclosure is intended in an illustrative rather than limiting sense, as it is contemplated that modifications will readily occur to those skilled in the art, within the spirit of the invention and the scope of the appended claims. It is further understood that the instant invention applies to all viruses infecting plants and plants generally and is not limited to those plasmids, viruses or plants described herein.

What is claimed is:

1. A system comprising:
   a replicon comprising:
   a tobamovirus-derived replication origin,
   at least one gene non-native to a tobamovirus and encoding a product non-native to the tobamovirus, and
   a gene encoding a tobamovirus-derived viral movement protein,
   wherein said replicon lacks a gene encoding a tobamovirus-derived replicase; and a tobamovirus-derived helper virus comprising:
   a gene encoding a tobamovirus-derived replicase, wherein said helper virus lacks a functional gene encoding the tobamovirus-derived viral movement protein; and wherein a DNA sequence of said replicon is integrated as a transgene in the chromosome of a plant cell which is susceptible to a tobamovirus.

2. The system of claim 1, wherein the sequence comprising the non-native gene in the replicon is located 5' to the 3' replication origin of the replicon.

3. The system of claim 1, wherein the DNA encoding the tobamovirus-derived viral movement protein is located 3' to the 5' replication origin of the replicon.

4. The system of claim 1, wherein the tobamovirus-derived viral movement protein is native to a TMV.

5. The system of claim 4, wherein the DNA encoding the TMV movement protein is located 3' to the 5' replication origin of the replicon.

6. The system of claim 1, wherein the gene non-native to the tobamovirus is expressed systemically in the presence of the tobamovirus-derived helper virus.

7. The system of claim 4, wherein the gene non-native to the tobamovirus is expressed systemically in the presence of the tobamovirus-derived helper virus.

8. A plant cell containing the system of claim 1.

9. A transgenic plant containing a system comprising:

a replicon comprising:

a tobamovirus-derived replication origin, at least one gene non-native to a tobamovirus and encoding a product non-native to the tobamovirus, and a gene encoding a tobamovirus-derived viral movement protein, wherein said replicon lacks a gene encoding a tobamovirus-derived replicase; and a tobamovirus-derived helper virus comprising:

a gene encoding a tobamovirus-derived replicase, wherein said helper virus lacks a functional gene encoding the tobamovirus-derived viral movement protein; and wherein a DNA sequence of said replicon is integrated as a transgene in the chromosome of a plant cell which is susceptible to a tobamovirus.

10. The transgenic plant of claim 9, wherein the sequence comprising the non-native gene in the replicon is located 5' to the 3' replication origin of the replicon.

11. The transgenic plant of claim 9, wherein the DNA encoding the tobamovirus-derived viral movement protein is located 3' to the 5' replication origin of the replicon.

12. The transgenic plant of claim 9, wherein the tobamovirus-derived viral movement protein is native to a TMV.

13. The transgenic plant of claim 12, wherein the DNA encoding the TMV movement protein is located 3' to the 5' replication origin of the replicon.

14. The transgenic plant of claim 9, wherein the gene non-native to the tobamovirus is expressed systemically in the presence of the tobamovirus-derived helper virus.

15. The transgenic plant of claim 12, wherein the gene non-native to the tobamovirus is expressed systemically in the presence of the tobamovirus-derived helper virus.

16. A method for expressing a protein in plants comprising:

(a) integrating a transgene into a chromosome of a plant cell suspectable to a tobamovirus, the transgene comprising a replicon which comprises:

a tobamovirus-derived replication origin, at least one gene non-native to a tobamovirus and encoding a protein product non-native to the tobamovirus, and a gene encoding a tobamovirus-derived viral movement protein, wherein said replicon lacks a gene encoding a tobamovirus-derived replicase; and (b) infecting the plant cell with a tobamovirus-derived helper virus comprising:

a gene encoding a tobamovirus-derived replicase, wherein said helper virus lacks a functional gene encoding the tobamovirus-derived viral movement protein; and wherein the protein product is expressed and accumulates in the plant cell.

17. The method of claim 16, wherein the sequence comprising the non-native gene in the replicon is located 5' to the 3' replication origin of the replicon.

18. The method of claim 16, wherein the DNA encoding the tobamovirus-derived viral movement protein is located 3' to the 5' replication origin of the replicon.

19. The method of claim 16, wherein the tobamovirus-derived viral movement protein is native to a TMV.

20. The method of claim 19, wherein the DNA encoding the TMV movement protein is located 3' to the 5' replication origin of the replicon.

* * * * *

UNITED STATES PATENT AND TRADEMARK OFFICE
CERTIFICATE OF CORRECTION

PATENT NO. : 5,811,653
DATED : September 22, 1998
INVENTOR(S) : Thomas H. Turpen, Vacaville, California It is certified that error appears in the above-identified patent and that said Letters Patent are hereby corrected as shown below:

Column 1, line 8, after "abandoned.", insert --This work was supported under National Science Foundation Grant No. 9561380.--

Signed and Sealed this

Third Day of April, 2001

Attest:

NICHOLAS P. GODICI

*Attesting Officer*     Acting Director of the United States Patent and Trademark Office